(12) United States Patent
Barbeau

(10) Patent No.: US 7,358,271 B2
(45) Date of Patent: Apr. 15, 2008

(54) SULPIRIDE PHARMACEUTICAL COMPOSITIONS

(75) Inventor: Donald L. Barbeau, Evanston, IL (US)

(73) Assignee: Williamsburg Holdings LLC, Evanston, IL (US)

( * ) Notice: Subject to any disclaimer, the term of this patent is extended or adjusted under 35 U.S.C. 154(b) by 543 days.

(21) Appl. No.: 10/933,771

(22) Filed: Sep. 4, 2004

(65) Prior Publication Data

US 2005/0080126 A1    Apr. 14, 2005

Related U.S. Application Data

(60) Provisional application No. 60/500,776, filed on Sep. 5, 2003.

(51) Int. Cl.
*A61K 31/40*    (2006.01)
*C07D 207/04*    (2006.01)

(52) U.S. Cl. ..................... 514/408; 548/571
(58) Field of Classification Search ................ 514/408; 548/571
See application file for complete search history.

(56) References Cited

U.S. PATENT DOCUMENTS 6,890,942 B2 *   5/2005   Walker et al. .............. 514/346

FOREIGN PATENT DOCUMENTS

WO    WO 2004/103278 A2    12/2004

OTHER PUBLICATIONS

Liu et al., Bioorganic &Medicinal Chemistry Letters 13 (2003), 3005-3007.*
Liu et al., "Acylsulfonamide-Containing PTP1B Inhibitors Designed to Mimic an Enzyme-Bound Water of Hydration", Bioorganic & Medicinal Chemistry Letters 13 (2003), pp. 3005-3007.
Baluom et al., "Improved intestinal absorption of sulpiride in rats with synchronized oral delivery systems", Journal of Controlled Release 70 (2001), pp. 139-147.
Naasani et al., "Improving the Oral Bioavailability of Sulpiride by Sodium Oleate in Rabbits", J. Pharm. Pharmacol, 1995, 47: pp. 469-473.
Kohri et al., "Improving the Oral Bioavailability of Sulpiride by a Gastric-retained Form in Rabbits", J. Pharm. Pharmacol, 1996, 48: pp. 371-374.

* cited by examiner

*Primary Examiner*—Kamal A Saeed
(74) *Attorney, Agent, or Firm*—Schiff Hardin LLP

(57) ABSTRACT

The present invention relates to pharmaceutical compositions containing sulpiride compounds having the general formula:

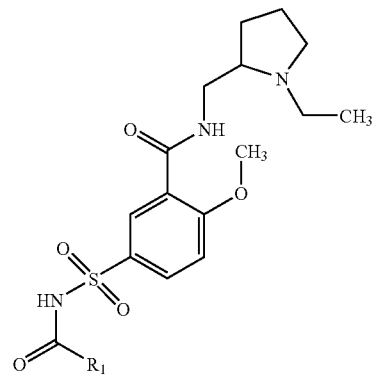

where $R_1$ is branched or straight chain alkyl having from 1 to about 7 carbon atoms, a substituted or unsubstituted aryl, a substituted or unsubstituted cycloalkyl, a substituted or unsubstituted aralkyl, a substituted or unsubstituted alkylcycloalkyl, or a group having the formula $(CH_2)_n R_2$ where $R_2$ is a substituted or unsubstituted aryl or a substituted or unsubstituted cycloalkyl, and n is an alkyl group having from 0 to about 6 carbon atoms and pharmaceutically acceptable salts or diluents.

16 Claims, No Drawings

SULPIRIDE PHARMACEUTICAL COMPOSITIONS

CROSS-REFERENCE TO RELATED APPLICATIONS

This patent application claims the benefit of prior filed copending provisional application No. 60/500,776 filed Sep. 5, 2003, titled Sulpiride Pharmaceutical Compositions.

BACKGROUND OF THE INVENTION

The present invention relates to pharmaceutical compositions containing sulpiride compounds having the general formula:

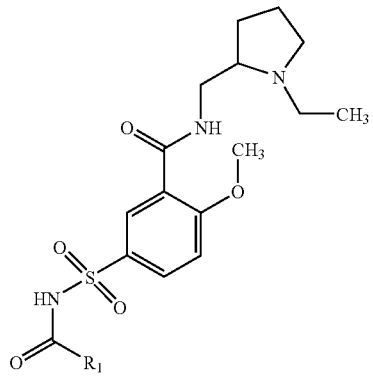

where $R_1$ is branched or straight chain alkyl having from 1 to about 7 carbon atoms, a substituted or unsubstituted aryl, a substituted or unsubstituted cycloalkyl, a substituted or unsubstituted aralkyl, a substituted or unsubstituted alkylcycloalkyl, or a group having the formula $(CH_2)_n R_2$ where $R_2$ is a substituted or unsubstituted aryl or a substituted or unsubstituted cycloalkyl, and n is an alkyl group having from 0 to about 6 carbon atoms.

Sulpiride is an atypical antipsychotic compound having antidepressant, antiemetic and prokinetic activity. Unlike other neuroleptic drugs, sulpiride is characterized by having a low incidence of extrapyramidal side effects. In particular, sulpiride is a substituted benzamide derivative that selectively inhibits dopamine $D_2$ receptors in the chemoreceptor trigger zone of the central nervous system (CNS) and in the enteric nervous system of the gastrointestinal tract. Levosulpiride is the levorotatory (S) enantiomer of sulpiride. Levosulpiride, with antiemetic and prokinetic effects, acts selectively by blocking the $D_2$ dopamine receptors in the CNS and in the peripheral submucosal and myenteric plexus of the gastrointestinal tract. The antiemetic effect of levosulpiride is due to inhibition of dopamine transmission and antagonism with $D_2$ receptors of the neurons in the area postrema of the vomiting center (IV ventricle) or chemoreceptor trigger zone in the CNS, blocking the inhibitory effect of dopamine on cholinergic neurons and therefore permitting a sustained cholinergic induced contraction of smooth muscle cell in the myenteric plexus of the esophagus, stomach, gallbladder, and intestine.

The antiemetic and prokinetic effects of levosulpiride are unique, and permit the treatment of a larger number of gastrointestinal disorders than other drugs in its class. Gastric hypomotility with delayed emptying of liquid and/or solid contents is a component of a number of gastrointestinal disorders. The symptoms of such disorders may include nausea, vomiting, heartburn, postprandial discomfort, indigestion, and gastroesophageal reflux. Gallbladder emptying has been also linked to the rate at which food enters the proximal duodenum. Clinical trials have demonstrated efficacy for levosulpiride in patients for functional dyspepsia (indigestion with accompanying nausea, vomiting and heartburn), GERD (gastroesophageal reflux disease), postoperative and chemotherapy-induced nausea and vomiting; and gastroparesis (diabetic gastric stasis) in diabetics.

A particularly important therapeutic property of levosulpiride in the treatment of chemotherapy-induced nausea and vomiting is that the use of dexamethasone is not required for its efficacy. Current approved drugs used to treat both acute and delayed chemotherapy-induced nausea and vomiting require the addition of dexamethasone to the treatment regimen in order to achieve an acceptable clinical outcome. Injectable levosulpiride treatment of chemotherapy-induced nausea and vomiting results in clinically superior efficacy over currently approved emetic agents, without requiring dexamethasone. Wu et al. have reported that dexamethasone pretreatment of cancer cell lines significantly inhibits chemotherapy-induced apoptosis in a glucocorticoid receptor-dependent manner (Wu W, Chaudhuri S, Brickley DR, Pang D, Karrison T, and Conzen SD, Cancer Research 64: 1757-1764 (2004)).

Despite its lack of side effects and its clinical efficacy without dexamethasone, the relative insolubility of levosulpiride in aqueous media has a significant impact on the formulation of both oral and parenteral dosage forms. Sulpiride is practically insoluble in water resulting in low absorption and bioavailability for the oral pharmaceutical formulations, and large injection volumes for the parenteral formulations. Moreover, because the pKa of levosulpiride is low, solubility in parenteral dosage forms requires the use of excipients having an extremely low pH. This, in turn, results in injectable products that have the potential to cause discomfort after injection to a patient.

Solubilization of water-insoluble drugs generally includes solubilization by pH control, by use of cosolvents, or by use of surfactants or complexation. The excipients used to solubilize drugs in oral and injectable dosage forms generally include pH modifiers, water-soluble organic solvents, water-insoluble organic solvents, surfactants and cyclodextrins.

Water-soluble drugs in oral dosage forms having a low molecular weight are normally well-absorbed as long as they are not degraded by the enzymes in the GI tract; however, many drugs are poorly soluble in water. Drugs which have a low solubility in water pose a tremendous challenge to pharmaceutical sciences. Adequate solubilization of such drugs with excipients which are biocompatible is a prerequisite to get the drug absorbed by the body after oral administration. After oral administration, these water-insoluble (lipophilic) drugs are confronted with the same uptake mechanisms as fatty components of food. They are solubilized by the bile juice, which contains phospholipids and bile salts which dissolve the lipophilic drugs in micellar structures. Incomplete or insufficient solubilization of drugs after oral administration often results in reduced absorption and corresponding reduced plasma bioavailability of the drug.

In the case of parenteral administration, these water-insoluble drugs usually contain co-solvents or adjustment of the carrier pH to solubilize the drug. These co-solvents and pH modifications can produce pain at the site of injection, or cause precipitation of drug at the site of administration that can have a marked effect on the blood concentration versus time profile.

For example, after intramuscular administration, the composition of the fluid in which the drug is dissolved is diluted by the fluid in the muscle, resulting in drug precipitating out at the site of injection. In order for absorption to take place, drug must redissolve through a slow process. As a consequence, administration of some drugs by the intramuscular route results in a slow release of drug from the site. If the dose administered is large enough, this can function as a sustained release preparation. However, if normal doses are given, the rise in drug concentration may be slowed to the degree that drug never achieves concentrations above the minimally effective concentration.

The currently available injectable formulation outside of the United States contains 25 mg of levosulpiride in 2 ml of water, sodium chloride and sulfuric acid. This formulation is generally administered at the following doses: 1 mg/kg iv (given 4-5 times) for chemotherapy-induced nausea and vomiting, and 50 to 100 mg iv for postsurgical nausea and vomiting.

The currently available oral formulation is a 25 mg tablet that is administered three times daily for a total daily dose of 75 mg/day for diabetic gastroparesis, GERD, and dyspepsia. Because sulpiride has limited aqueous solubility, the oral formulations suffer from a reduced absorption in the gastrointestinal tract (~30%) and resultant low bioavailability. Because orally administered levosulpiride is absorbed predominantly from the upper part of the small intestine; the drug has a small absorption window in the gastrointestinal tract. Unless levosulpiride is taken with food, the transit time of levosulpiride along the upper portion of the small intestine reduces the opportunity for the drug to be absorbed from the effective site of absorption. A study in healthy volunteers has shown that the decreased emptying rate of sulpiride from the stomach after food permits more contact time between sulpiride and its absorption sites in the intestine, and increases absorption. Food was shown to increase the bioavailability in these subjects from 20 to 27%. Consequently, the drug is dosed three times daily with meals.

It is an object of the present invention to provide pharmaceutical compositions containing aryl and alkyl derivatives of sulpiride compounds having improved physiochemical properties.

It is a further object of the present invention to provide water-soluble aryl and alkyl derivatives of sulpiride and pharmaceutical compositions thereof.

It is a further object of the present invention to provide aryl and alkyl derivatives of sulpiride compounds having improved aqueous solubility over sulpiride.

It is a further object of the present invention to provide pharmaceutical compositions containing aryl and alkyl derivatives of sulpiride compounds having improved oral absorption of sulpiride in the upper portion of the small intestine.

It is a further object of the present invention to provide aryl and alkyl derivatives of sulpiride pharmaceutical compounds having improved injectable formulation properties.

BRIEF SUMMARY OF THE INVENTION

This invention relates to compounds having the formula:

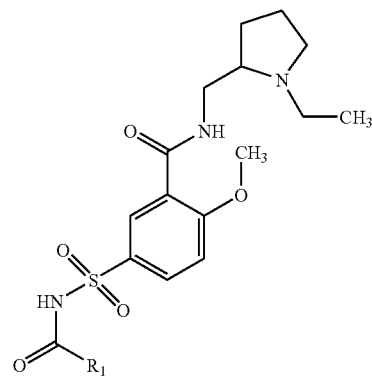

where $R_1$ is branched or straight chain alkyl having from 1 to about 7 carbon atoms, a substituted or unsubstituted aryl, a substituted or unsubstituted cycloalkyl, a substituted or unsubstituted aralkyl, a substituted or unsubstituted alkylcycloalkyl, or a group having the formula $(CH_2)_n R_2$ where $R_2$ is a substituted or unsubstituted aryl or a substituted or unsubstituted cycloalkyl, and n is an alkyl group having from 0 to about 6 carbon atoms, or a pharmaceutically acceptable salt thereof.

DETAILED DESCRIPTION OF THE INVENTION

Compounds in accordance with the one embodiment of the present invention are represented by the formula:

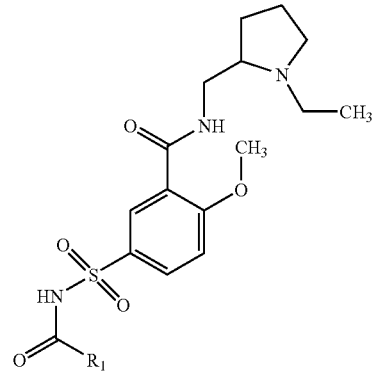

where $R_1$ is branched or straight chain alkyl having from 1 to about 7 carbon atoms, a substituted or unsubstituted aryl, a substituted or unsubstituted cycloalkyl, a substituted or unsubstituted aralkyl, a substituted or unsubstituted alkylcycloalkyl, or a group having the formula $(CH_2)_n R_2$ where $R_2$ is a substituted or unsubstituted aryl or a substituted or unsubstituted cycloalkyl, and n is an alkyl group having from 0 to about 6 carbon atoms.

In one aspect of the present invention, $R_1$ is preferably an unsubstituted branched or straight chain lower alkyl group including but not limited to methyl, ethyl, propyl, isopropyl, butyl, isobutyl, pentyl, isopentyl and hexyl. In a preferred embodiment of the present invention, $R_1$ is a straight chain lower alkyl having from 1 to about 6 carbon atoms. In a more preferred embodiment of the present invention, $R_1$ is methyl, ethyl or propyl.

In another aspect of the present invention, compounds of the present invention are represented by the formula:

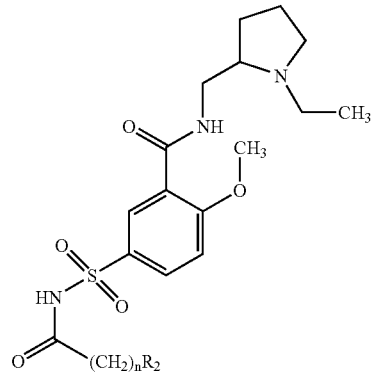

where $R_2$ is a substituted or unsubstituted aryl or a substituted or unsubstituted cycloalkyl, and n is an alkyl group having from 0 to about 6 carbon atoms.

Illustrative compounds in accordance with the present invention include the following:

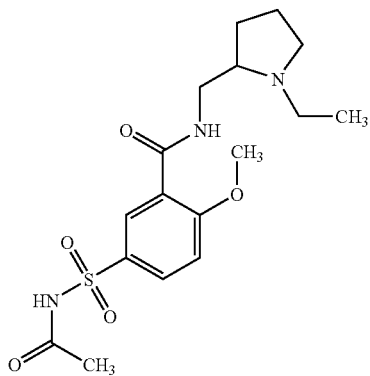

5-Acetylsulfamoyl-N-(1-ethyl-pyrrolidin-2-ylmethyl)-2-methoxy-benzamide

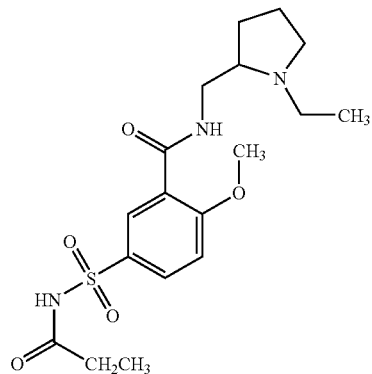

N-1-Ethyl-pyrrolidin-2-ylmethyl)-2-methoxy-5-propionylsulfamoyl-benzamide

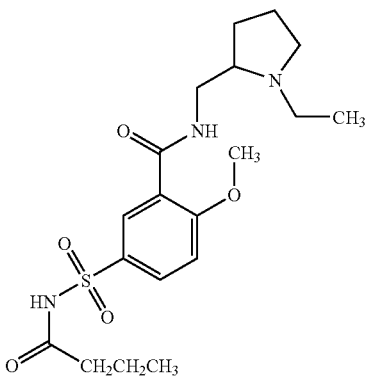

5-Butyrylsulfamoyl-N-(1-ethyl-pyrrolidin-2-ylmethyl)-2-methoxy-benzami

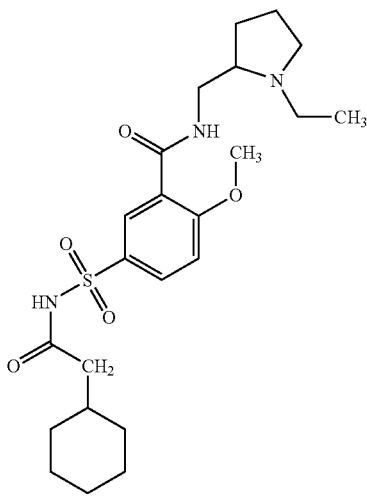

5-(Cyclohexanecarbonyl-sulfamoyl)-N-(1-ethyl-pyrrolidin-2-ylmethyl)-2-methoxy-benzamide

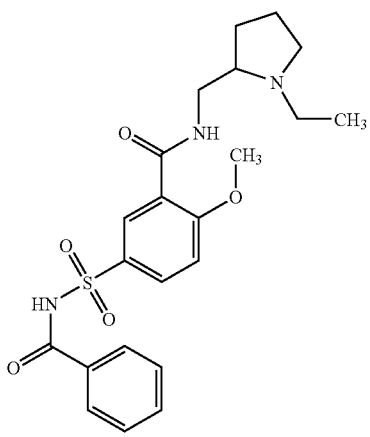

5-Benzoylsulfamoyl-N-(1-ethyl-pyrrolidin-2-ylmethyl)-2-ethoxy-benzamide

Compounds in accordance with the present invention are readily prepared by acylation of the sulfonamide with an anhydride in the presence of triethylamine as shown below:

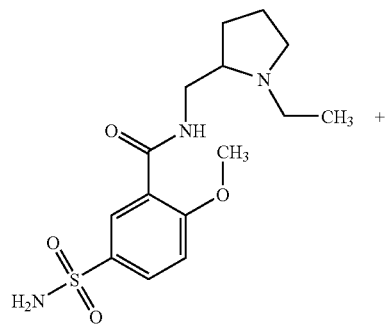

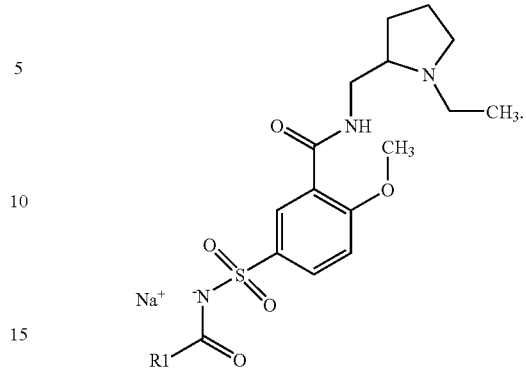

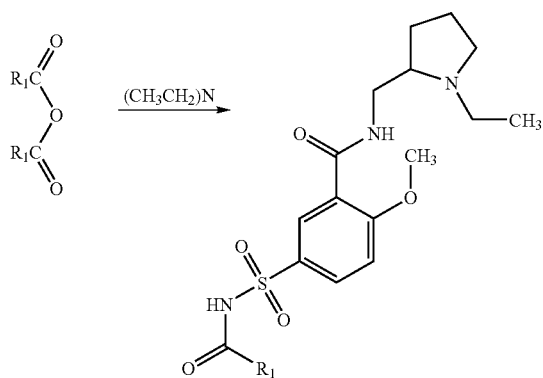

The compounds of the present invention differ from levosulpiride in some respects and are similar to levosulpiride in others. The compounds of the present invention differ structurally from the pharmaceutically active parent sulpiride moiety by the presence of acyl amine derivatives. The compounds of the present invention also differ physicochemically from the pharmaceutically active parent sulpiride moiety by their ionizing properties. For example, the pKa of sulpiride is lower than physiological pH and thus requires a very low pH for solubilization of the drug in its aqueous dosage form. On the other hand, the pKa of the sulpiride compounds of the present invention is considerably higher than physiological pH such that these compounds are soluble in an aqueous dosage form at or near physiological pH. The compounds of the present invention are similar to levosulpiride with respect to their lipophilicity (log P) and their pharmacological activity. It is expected that the conversion of the compounds in accordance with the present invention to active sulpiride or levosulpiride is rapid and complete once the drug reaches the plasma. As prodrugs, the compounds of the present invention are converted to the active moiety, sulpiride or levosulpiride, after both oral and intravenous administration.

Pharmaceutically acceptable salts are well known in the art. A preferred salt of the compounds in accordance with the present invention is the sodium salt as shown below:

The sodium salts of the compounds in accordance with the present invention can be prepared by titration of the acylated sulfonamide with aqueous sodium hydroxide.

EXAMPLE 1

Preparation of 5-Acetylsulfamoyl-N-(1-ethyl-pyrrolidin-2-ylmethyl)-2-methoxy-benzamide A solution of N-(1-Ethyl-pyrrolidin-2-ylmethyl)-2-methoxy-5-sulfamoyl-benzamide, acetic anhydride and triethylamine are reacted at room temperature, diluted with water and extracted with ethyl acetate. The ethyl acetate layer is dried, filtered and concentrated under vacuum, and the residue recrystallized from ethyl acetate.

EXAMPLE 2

Preparation of 5-Acetylsulfamoyl-N-(1-ethyl-pyrrolidin-2-ylmethyl)-2-methoxy-benzamide, sodium salt A solution of 5-Acetylsulfamoyl-N-(1-ethyl-pyrrolidin-2-ylmethyl)-2-methoxy-benzamide in ethanol and water is treated with sodium hydroxide, concentrated in vacuum to produce the sodium salt 5-Acetylsulfamoyl-N-(1-ethyl-pyrrolidin-2-ylmethyl)-2-methoxy-benzamide.

EXAMPLE 3

Preparation of N-1-Ethyl-pyrrolidin-2-ylmethyl)-2-methoxy-5-propionylsulfamoyl-benzamide A solution of N-(1-Ethyl-pyrrolidin-2-ylmethyl)-2-methoxy-5-sulfamoyl-benzamide, propionic anhydride and triethylamine are reacted at room temperature, diluted with water and extracted with ethyl acetate. The ethyl acetate layer is dried, filtered and concentrated under vacuum, and the residue recrystallized from ethyl acetate.

EXAMPLE 4

Preparation of N-1-Ethyl-pyrrolidin-2-ylmethyl)-2-methoxy-5-propionylsulfamoyl-benzamide, sodium salt.

A solution of N-1-Ethyl-pyrrolidin-2-ylmethyl)-2-methoxy-5-propionylsulfamoyl-benzamide in ethanol and water is treated with sodium hydroxide, concentrated in vacuum to produce the sodium salt N-1-Ethyl-pyrrolidin-2-ylmethyl)-2-methoxy-5-propionylsulfamoyl-benzamide.

The present invention has been described in detail using specific examples to illustrate the preferred embodiments of the invention; however, it will be obvious to those skilled in the art that various modifications thereto can be made without departing from the spirit and scope thereof.

I claim:
1. A compound having the formula:

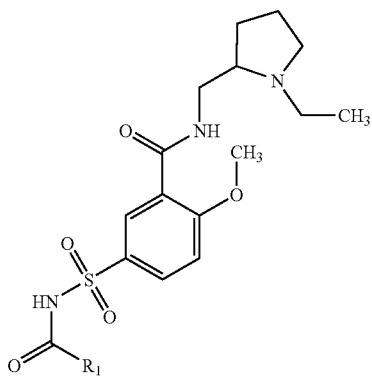

where $R_1$ is branched or strain chain alkyl having from 1 to about 7 carbon atoms, an unsubstituted aryl, a substituted or unsubstituted cycloalkyl, a substituted or unsubstituted aralkyl, a substituted or unsubstituted alkylcycloalkyl, or a group having the formula $(CH_2)_nR_2$ where $R_2$ is a substituted or unsubstituted aryl or a substituted or unsubstituted cycloalkyl, and n is an alkyl group having from 0 to about 6 carbon atoms,
or a pharmaceutically acceptable salt thereof.

2. The compound of claim 1, wherein $R_1$ is methyl, ethyl, propyl, isopropyl, butyl, isobutyl, pentyl, isopentyl or hexyl.

3. The compound of claim 1, wherein $R_1$ is a straight chain lower alkyl having from 1 to about 6 carbon atoms.

4. The compound of claim 3, wherein $R_1$ is methyl, ethyl, or propyl.

5. The compound of claim 1, 2 or 3, wherein the compound is the levorotary isomer.

6. A pharmaceutical composition comprising a compound having the formula:

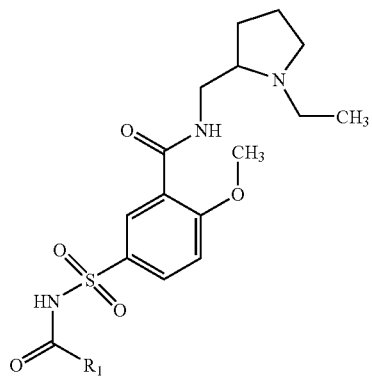

where $R_1$ is branched or strain chain alkyl having from 1 to about 7 carbon atoms, an unsubstituted aryl, a substituted or unsubstituted cycloalkyl, a substituted or unsubstituted aralkyl, a substituted or unsubstituted alkylcycloalkyl, or a group having the formula $(CH_2)_nR_2$ where $R_2$ is a substituted or unsubstituted aryl or a substituted or unsubstituted cycloalkyl, and n is an alkyl group having from 0 to about 6 carbon atoms and
a pharmaceutically acceptable salt or diluent.

7. The pharmaceutical composition of claim 6, wherein $R_1$ is methyl, ethyl, propyl, isopropyl, butyl, isobutyl, pentyl, isopentyl or hexyl.

8. The compound of claim 7, wherein $R_1$ is a straight chain lower alkyl having from 1 to about 6 carbon atoms.

9. The compound of claim 8, wherein $R_1$ is methyl, ethyl, or propyl.

10. The compound of claim 6, 7 or 8, wherein the compound is the levorotary isomer.

11. The composition of claim 6 wherein said compound has the formula

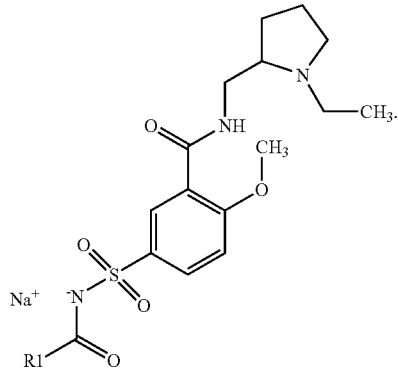

12. The composition of claim 10 wherein said compound has the formula

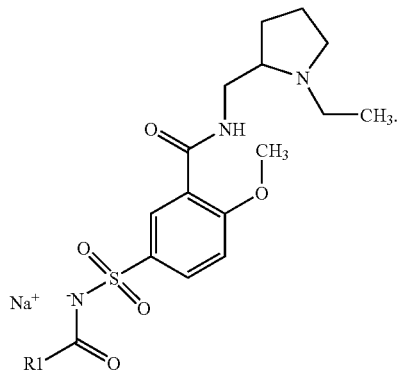

13. The composition of claim 11 wherein said composition is a parenteral formulation.

14. The composition of claim 11 wherein said composition is an oral formulation.

15. The composition of claim 12 wherein said composition is a parenteral formulation.

16. The composition of claim 12 wherein said composition is an oral formulation.

* * * * *